(12) United States Patent
Aburai et al.

(10) Patent No.: US 9,156,762 B2
(45) Date of Patent: Oct. 13, 2015

(54) 4,4-BIS[(ETHENYLOXY)METHYL] CYCLOHEXENE AND METHOD FOR PRODUCING SAME

(75) Inventors: Youhei Aburai, Kanagawa (JP);
Shinichi Kakinuma, Kanagawa (JP);
Masahiro Murotani, Kanagawa (JP)

(73) Assignee: Nippon Carbide Industries Co., Inc. (JP)

( * ) Notice: Subject to any disclaimer, the term of this patent is extended or adjusted under 35 U.S.C. 154(b) by 171 days.

(21) Appl. No.: 14/114,434

(22) PCT Filed: Apr. 10, 2012

(86) PCT No.: PCT/JP2012/059809
§ 371 (c)(1),
(2), (4) Date: Oct. 28, 2013

(87) PCT Pub. No.: WO2012/147511
PCT Pub. Date: Nov. 1, 2012

(65) Prior Publication Data
US 2014/0058136 A1     Feb. 27, 2014

(30) Foreign Application Priority Data

Apr. 28, 2011  (JP) .................. 2011-102215

(51) Int. Cl.
*C07C 43/162* (2006.01)
*C07C 41/08* (2006.01)

(52) U.S. Cl.
CPC ............... *C07C 43/162* (2013.01); *C07C 41/08* (2013.01); *C07C 2101/16* (2013.01)

(58) Field of Classification Search
None
See application file for complete search history.

(56) References Cited

FOREIGN PATENT DOCUMENTS

| JP | S57-171930 A | 10/1982 |
|---|---|---|
| JP | H07-82514 A | 3/1995 |
| JP | 2001-278829 A | 10/2001 |
| JP | 2005-023049 A | 1/2005 |
| JP | 2009-242484 A | 10/2009 |
| JP | 2010-053087 A | 3/2010 |
| WO | WO-2010/137742 A1 | 12/2010 |
| WO | WO-2011/136355 A1 | 11/2011 |
| WO | WO-2012/046880 A1 | 4/2012 |

OTHER PUBLICATIONS

International Search Report, mailed on Jul. 17, 2012.

*Primary Examiner* — Rosalynd Keys
(74) *Attorney, Agent, or Firm* — Fishman Stewart Yamaguchi PLLC

(57) ABSTRACT

A novel substance, 4,4-bis[(ethenyloxy)methyl]cyclohexene having the formula (I), which is low in odor, low in volatility, and low in skin irritability, and therefore, can be used as, for example, a starting material for inks and a starting material for electronic materials, and a method for producing the same are provided:

Formula (I):

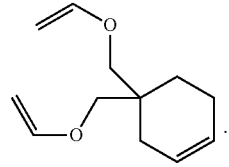

5 Claims, 2 Drawing Sheets

4,4-BIS[(ETHENYLOXY)METHYL]CYCLOHEXENE AND METHOD FOR PRODUCING SAME

TECHNICAL FIELD

The present invention relates to a novel vinyl ether, 4,4-bis[(ethenyloxy)methyl]cyclohexene and a method for producing the same.

BACKGROUND ART

The divinyl ether compound according to the present invention, specifically 4,4-bis[(ethenyloxy)methyl]cyclohexene (other name: 3-cyclohexene-1,1-dimethanol divinyl ether), has not been reported in the past and is believed to be a novel compound.

As technology relating to divinyl ether compounds such as the present invention, for example, there are the following Patent Literatures 1 and 2. Patent Literature 1 describes pentaerythritolacetal divinyl ether. This compound has an acetal structure, and therefore, easily hydrolyzes and differs from the divinyl ether compound according to the present invention in the point of stability against water. Patent Literature 2 describes 1,3-adamantane dimethanol divinyl ether, but this compound differs from the divinyl ether compound according to the present invention in the point of ease of cyclization polymerization.

CITATIONS LIST

Patent Literature

Patent Literature 1: Japanese Patent Publication No. 2009-242484A

Patent Literature 2: Japanese Patent Publication No. 2010-053087A

SUMMARY OF INVENTION

Problem to be Solved by the Invention

An object of the present invention is to provide 4,4-bis[(ethenyloxy)methyl]cyclohexene having the formula (I):

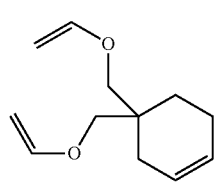

(I)

Means for Solving the Problems

In accordance with the present invention, it is possible to obtain a novel vinyl ether by the method for producing 4,4-bis[(ethenyloxy)methyl]cyclohexene represented by the formula (I):

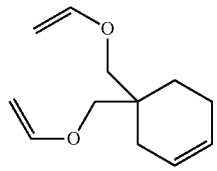

(I)

by reacting 4,4-bis[(hydroxy)methyl]cyclohexene represented by the formula (II):

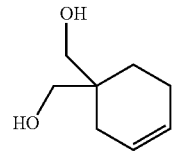

(II)

and acetylene in the presence of an alkali compound in an aprotonic polar solvent. The resultant 4,4-bis[(ethenyloxy)methyl]cyclohexene is low in odor, low in volatility, and low in skin irritability, and therefore, can be used as, for example, a starting material for inks and a starting material for electronic materials.

Advantageous Effects of Invention

The compound, 4,4-bis[(ethenyloxy)methyl]cyclohexene (hereinbelow, sometimes simply abbreviated as "vinyl ether (I)") according to the present invention is characterized by having two vinyl ether groups at specific positions and having special reactivity alone or with other compounds. The vinyl ether (I) according to the present invention is low in odor, low in volatility, and low in skin irritability and is excellent in curability, substrate adhesion, and light transmission in the ultraviolet region, and, therefore can be expected to be useful as a starting material for inks and a starting material for electronic materials. Accordingly, the 4,4-bis[(ethenyloxy)methyl]cyclohexene according to the present invention is useful as a cross-linking agent and various synthesizing reagents and can be utilized as a starting material for inks such as for inks and paints and as a starting material for electronic materials such as resists, color filters, adhesives, printing materials, sealants, and image forming agents.

MODE FOR CARRYING OUT THE INVENTION

Figure 1:
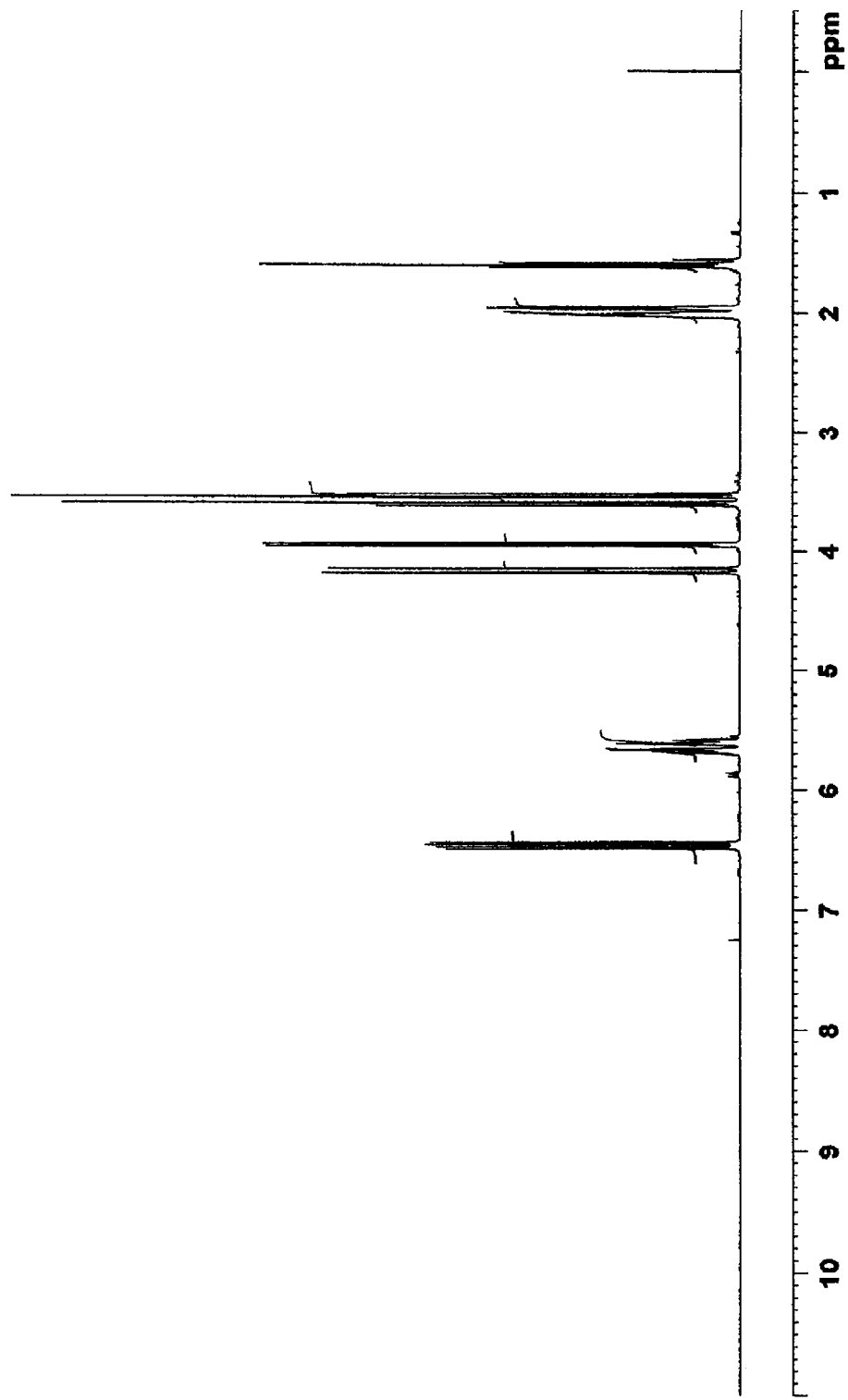
FIG. 1 is an $^1$H NMR chart of the 4,4-bis[(ethenyloxy)methyl]cyclohexene prepared in Example 1.

The present invention will now be explained in further detail.

The vinyl ether (I) according to the present invention can be produced according to the following reaction formula:

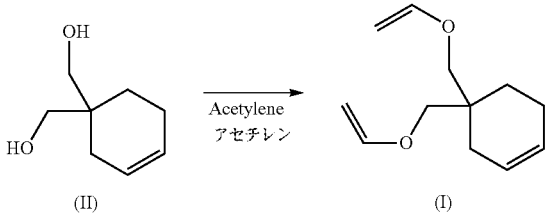

As a specific method for the synthesis of the vinyl ether (I) according to the present invention, for example, the following method may be mentioned.

A reaction vessel such as an SUS (stainless steel) pressure resistant reaction vessel is charged with, as a solvent, an aprotonic polar solvent such as, for example, one or more solvents selected from dimethylsulfoxide, N-methylpyrrolidone, N,N'-dimethylethylene urea, N,N'-diethylethylene urea, N,N'-dipropylethylene urea, N,N'-diisopropylethylene urea, N,N'-dibutylethylene urea, N,N'-dimethylpropylene urea, N,N'-diethylpropylene urea, N,N'-dipropylpropylene urea, N,N'-diisopropylpropylene urea, N,N'-dibutylpropylene urea, N,N,N',N',N'',N''-hexamethylphosphoric acid triamide, 1,3,4-trimethyl-2-imidazolidinone, ethylene glycol dimethyl ether, ethylene glycol diethyl ether, ethylene glycol dipropyl ether, ethylene glycol diisopropyl ether, ethylene glycol dibutyl ether, diethylene glycol dimethyl ether, diethylene glycol diethyl ether, diethylene glycol dipropyl ether, diethylene glycol diisopropyl ether, diethylene glycol dibutyl ether, triethylene glycol dimethyl ether, triethylene glycol diethyl ether, triethylene glycol dipropyl ether, triethylene glycol diisopropyl ether, triethylene glycol dibutyl ether, tetraethylene glycol dimethyl ether, tetraethylene glycol diethyl ether, tetraethylene glycol dipropyl ether, tetraethylene glycol diisopropyl ether, tetraethylene glycol dibutyl ether, polyethylene glycol dimethyl ether, polyethylene glycol diethyl ether, polyethylene glycol dipropyl ether, polyethylene glycol diisopropyl ether, and polyethylene glycol dibutyl ether, etc., and then charged with the starting compound, 4,4-bis[(hydroxy)methyl]cyclohexene, and charged with a reaction catalyst comprised of an alkaline compound such as an alkali metal hydroxide (e.g., potassium hydroxide, sodium hydroxide, rubidium hydroxide, and cesium hydroxide), an alcoholate prepared from an alkali metal hydroxide and the starting material alcohol (II). The amount of use of the reaction catalyst comprised of the alkaline compound is not particularly limited, but the amount of use is preferably 2 parts by weight or more, more preferably 4 to 50 parts by weight, based upon 100 parts by weight of the 4,4-bis[(hydroxy)methyl]cyclohexene.

In the method of the present invention, from the viewpoints of the solubility of the starting material, the productivity and the reaction rate, an aprotonic polar solvent is preferably used. The amount of use of the aprotonic polar solvent is not particularly limited, but the amount of use is preferably 100 to 1,000 parts by weight, more preferably 200 to 700 parts by weight, based upon to 100 parts by weight of the 4,4-bis[(hydroxy)methyl]cyclohexene. If the amount of use of the aprotonic polar solvent is less than 100 parts by weight, based upon 100 parts by weight of the 4,4-bis[(hydroxy)methyl]cyclohexene, the selectivity of the reaction is liable to be decreased. On the other hand, if the amount of use of the aprotonic polar solvent is more than 1000 parts by weight, based upon 100 parts by weight of the 4,4-bis[(hydroxy)methyl]cyclohexene, the removal of the solvent after the end of the reaction is liable to become troublesome.

Next, the inside of the reaction vessel, is replaced with an inert gas such as nitrogen gas then the reaction vessel is sealed and, while acetylene is pumped in, the temperature is increased to cause the reaction, whereby the 4,4-bis[(ethenyloxy)methyl]cyclohexene according to the present invention can be produced. The atmosphere in the reaction vessel can be made acetylene alone, but it is also possible to use acetylene which is diluted with an inert gas such as nitrogen, helium, argon.

Regarding the reaction conditions for producing the 4,4-bis[(ethenyloxy)methyl]cyclohexene according to the present invention, if both the reaction temperature and the reaction pressure (the acetylene partial pressure) are made high, the reaction rate will increase, but the safety will decrease. Further, if the reaction temperature is high, side reactions are liable to progress. For example, the pressure of the acetylene is preferably a gauge pressure of 0.01 MPa or more. From the viewpoint of the productivity, the suppression of side reactions, and the safety, the pressure of the acetylene is more preferably a gauge pressure of 0.15 MPa to 1.0 MPa. On the other hand, the reaction temperature is preferably 80 to 180° C. From the viewpoint of the reaction rate, 100° C. or more is more preferable. From the viewpoint of the economy and the suppression of side reactions, 130° C. or less is more further preferable.

Note that, the starting compound, 4,4-bis[(hydroxy)methyl]cyclohexene (II) in the present invention can be produced by a conventionally method. It may be produced by the method described in, for example, Japanese Patent Publication No. 57-45179A, specifically the method for reacting 3-cyclohexene-1-carboaldehyde with formaldehyde in an alkaline solution after through methylolation and a Cannizzaro reaction, 4,4-bis[(hydroxy)methyl]cyclohexene is obtained. Note that, 4,4-bis[(hydroxy)methyl]cyclohexene (II) is available, as a commercial product, from J&K Scientific Ltd. (China).

EXAMPLES

Examples of the present invention will now be shown, but the scope of the present invention is not limited to these Examples needless to say.

Preparation Example 1

To a 5-liter volume four-necked flask provided with a stirrer, a thermometer, a Dimroth condenser and a dropping funnel, 633.3 g (purity 92%, 19 mol) of paraformaldehyde dissolved in 1004.0 g of water was charged, 465.6 g of sodium hydroxide (purity 98.5%, 11.5 mol) dissolved in 1397.0 g of water were dropwise added. Next, the mixture was cooled in an ice bath to 10° C. and 880.7 g of 3-cyclohexene-1-carboaldehyde (purity 97%, 7.8 mol) was dropwise added over 1 hour to the mixture. After dropwise addition, the solution temperature was increased to 20° C. The mixture was stirred at that temperature for 1 hour, then the flask was immersed in a hot water bath and was further stirred at 55° C. for 1 hour. Next, the reaction mixture was cooled down to 15° C. in a water bath and the precipitated solid was obtained by filtration. The solid thus obtained was washed with water to obtain a wet crude crystal of 4,4-bis[(hydroxy)methyl]cyclohexene (II) in an amount of 1396.0 g.

A part of the wet crude crystal of 4,4-bis[(hydroxy)methyl]cyclohexene (II) obtained above was rinsed with water, the acetone insolubles were filtered out, then the resultant mixture was recrystallized with a weight ratio of the crude crystals:acetone of about 1:4. The resultant mixture was further rinsed with water and recrystallized with acetone, then was dried in vacuo to obtain a crystal of 4,4-bis[(hydroxy)methyl]cyclohexene in an amount of 55.6 g (purity by gas chromatography: 99.9%). This was used in the following Example 1.

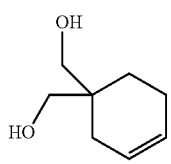

(II)

The results of analysis by NMR of the 4,4-bis[(hydroxy)methyl]cyclohexene (II) obtained were as follows.

$^1$H NMR (CDCl$_3$, TMS, 400 MHz): δ ppm 1.56 (t, 2H, J=6.4 Hz), 1.81 (quin, 2H, J=2.7 Hz), 2.03 (m, 2H), 3.24 (brs, 2H), 3.59 (s, 4H), 5.60 (m, 1H), 5.69 (m, 1H)

$^{13}$C NMR (CDCl$_3$, TMS, 100 MHz): δ ppm 21.6, 25.7, 29.4, 37.3, 69.4, 124.5, 126.6

Example 1

To a 300 ml volume SUS pressure resistant reaction vessel provided with a stirrer, a pressure gauge, a thermometer, a gas introduction tube and a gas purge line an aprotic polar solvent comprised of 160.1 g of dimethylsulfoxide, 40.1 g (0.28 mol) of the 99.9% purity of 4,4-bis[(hydroxy)methyl]cyclohexene obtained in the Preparation Example 1, and, as a reaction catalyst comprised of an alkaline compound, 2.53 g (0.043 mol) of 95.0% purity of potassium hydroxide were introduced. While stirring, nitrogen gas was purged for about 60 minutes to replace the inside of the vessel with nitrogen. Next, the reaction vessel was sealed, then the vessel was charged with acetylene gas at 0.18 MPa pressure. Next, while holding the gauge pressure at 0.18 MPa, the temperature was gradually increased. The reaction was continued for about 6 hours and 30 minutes after the temperature inside the reaction vessel exceeded 80° C. During this time, 4.10 g (0.069 mol) of 95.0% purity of potassium hydroxide was added to the reaction vessel. Acetylene gas was suitably replenished to maintain the inside pressure of the reaction vessel constantly at 0.18 MPa. The inside temperature of the reaction vessel was controlled to 105° C. or less. After the end of the reaction, the residual acetylene gas was purged to obtain 204.8 g of a reaction solution. The resultant reaction solution was analyzed by gas chromatography. As a result, the disappearance of the peak derived from 4,4-bis[(hydroxy)methyl]cyclohexene was confirmed.

Next, the reaction solvent was removed from the reaction solution and the remainder was distilled under reduced pressure (0.4 to 0.5 kPa) to obtain 43.2 g of a fraction distilled at 80° C. to 81° C. The fraction thus obtained was analyzed by NMR. The resultant product was the 4,4-bis[(ethenyloxy) methyl]cyclohexene shown by the following formula (I) (purity by gas chromatography 99.2%, yield 78.4%).

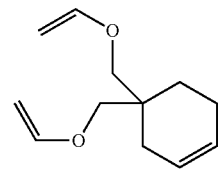

(I)

Figure 2:
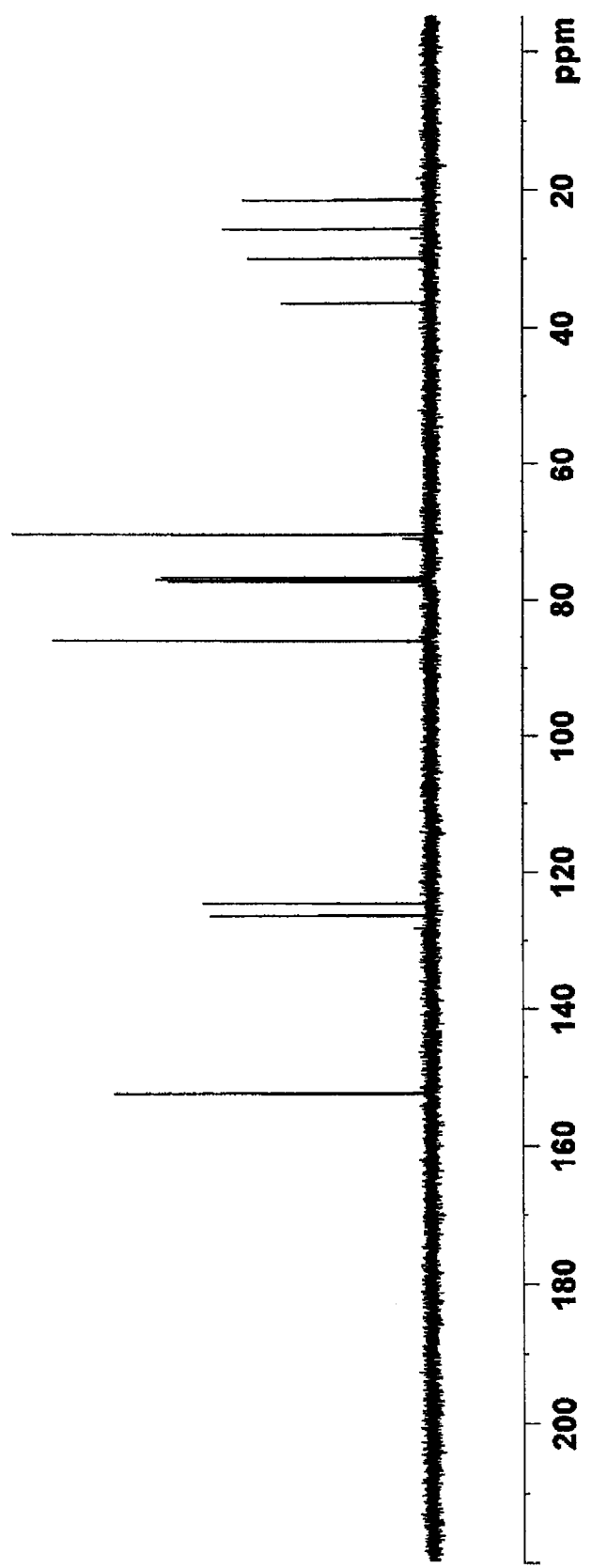
FIG. 2 is a $^{13}$C NMR chart of the 4,4-bis[(ethenyloxy)methyl]cyclohexene prepared in Example 1.

The 4,4-bis[(ethenyloxy)methyl]cyclohexene obtained above was analyzed by NMR. The results are shown in Table 1 and FIG. 1 and FIG. 2.

TABLE 1

| $^1$H NMR (CDCl$_3$, TMS, 400 MHz) | | | | $^{13}$C NMR (CDCl$_3$, TMS, 100 MHz) | |
|---|---|---|---|---|---|
| 6.47 ppm | dd = 6.8, 14.3 Hz | 2H | CH$_2$=CH—O | 152.3 ppm | CH$_2$=CH—O |
| 5.68 ppm | m | 1H | CH=CH (in ring) | 126.4 ppm | CH=CH (in ring) |
| 5.61 ppm | m | 1H | CH=CH (in ring) | 124.6 ppm | CH=CH (in ring) |
| 4.17 ppm | dd = 1.9, 14.3 Hz | 2H | CH$_2$=CH—O | 86.1 ppm | CH$_2$=CH—O |
| 3.95 ppm | dd = 1.9, 6.8 Hz | 2H | CH$_2$=CH—O | | |
| 3.61 ppm | d = 9.6 Hz | 2H | CH$_2$—O | 70.4 ppm | CH$_2$—O |
| 3.54 ppm | d = 9.6 Hz | 2H | CH$_2$—O | | |
| | | | | 36.5 ppm | C |
| 2.02 ppm | m | 2H | CH$_2$—CH$_2$—C— | 21.5 ppm | CH$_2$ |
| 1.96 ppm | quin = 2.7 Hz | 2H | CH$_2$—CH$_2$—C— | 29.9 ppm | CH$_2$ |
| 1.61 ppm | t = 6.4 Hz | 2H | CH—CH$_2$—C— | 25.7 ppm | CH$_2$ |

Application Example 1

The 4,4-bis[(ethenyloxy)methyl]cyclohexene obtained in Example 1 was polymerized as follows:

As the polymerization initiator and Lewis acid, HCl/ZnCl$_2$ were used. As the solvent, methylene chloride was used. A Schlenk flask was charged with 4.0 ml of 4,4-bis[(ethenyloxy)methyl]cyclohexene solution, 0.5 ml of 0.18% HCl solution and 0.5 ml of ZnCl$_2$ solution in thus order with a syringe to start the polymerization. This was performed in methylene chloride at −30° C., a monomer concentration of 0.15 mol/liter, an HCl concentration of 5.0 mmol/liter, and an ZnCl$_2$ concentration at 2.0 mmol/liter. The polymerization was stopped in 25 minutes, when the polymerization rate reached 98% by adding methanol containing a small amount of aqueous ammonia to the polymerization system.

The solution stopped in polymerization was transferred to a separating funnel and was diluted with methylene chloride, and was washed with an aqueous sodium chloride saturated solution (ion-exchanged water) three times. Next, the solvent was removed from the organic layer by an evaporator and the remainder was dried in vacuo to recover the produced polymer.

This polymer was further purified by decantation with methanol. The polymer thus obtained had a number average molecular weight M$_n$ of 4290, a molecular weight distribution (M$_w$/M$_n$) of 1.42, a glass transition temperature (Tg) of 103° C., and a thermal decomposition temperature (Td) of 347° C. Note that the analysis was performed using a differential scanning calorimeter device (RIGAKU Thermo Plus DSC8230L).

When the divinyl ether homopolymer obtained in Application Example 1 was used as a starting material for an ink, the resultant product was low in the odor, low in the volatility, and low in the skin irritability. Further, the glass transition temperature was high and, therefore, excellent performance was exhibited.

When the divinyl ether homopolymer obtained in Application Example 1 was used as a starting material for a paint, the resultant mixture was low in the odor, low in the volatility, and low in the skin irritability. Further, the glass transition temperature was high and, therefore, a coating film which was high in the hardness and excellent in the dryability and stain resistance was obtained. Further, when this was used as a starting material for electronic materials, the resultant product was low in the odor, low in the volatility, and low in the skin irritability. Further, since the glass transition temperature was high, excellent performance was exhibited. Further, when this was used as a starting material for a photoresist, the resultant product was low in the odor, low in the volatility, and low in the skin irritability. Further, since the glass transition temperature was high, a resist having a good strength could be obtained.

INDUSTRIAL APPLICABILITY

By polymerizing 4,4-bis[(ethenyloxy)methyl]cyclohexene to obtain a divinyl ether homopolymer, the excellent performance of a high glass transition temperature is exhibited. Further, the curability, substrate adhesion, and transparency are excellent and, in addition, the heat resistance is excellent, and, therefore, the divinyl ether homopolymer is useful as a starting material for inks such as for inks and paints and as a starting material for electronic materials such as resists, color filters, adhesives, printing materials, sealants, and image forming agents.

The invention claimed is:

1. 4,4-bis[(ethenyloxy)methyl]cyclohexene represented by the formula (I):

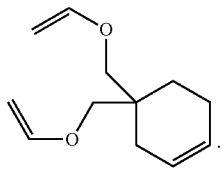

(I)

2. A method for producing 4,4-bis[(ethenyloxy)methyl]cyclohexene represented by the formula (I):

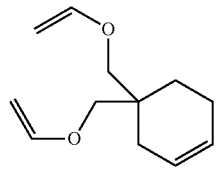

(I)

comprising reacting 4,4-bis[(hydroxy)methyl]cyclohexene represented by the formula (II):

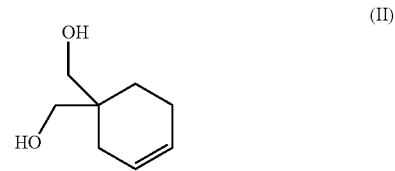

(II)

and acetylene in the presence of an alkaline compound in an aprotonic polar solvent.

3. The method as claimed in claim 2, wherein the aprotonic polar solvent includes one or more solvents selected from dimethylsulfoxide, N-methylpyrrolidone, N,N'-dimethylethylene urea, N,N'-diethylethylene urea, N,N'-dipropylethylene urea, N,N'-diisopropylethylene urea, N,N'-dibutylethylene urea, N,N'-dimethylpropylene urea, N,N'-diethylpropylene urea, N,N'-dipropylpropylene urea, N,N'-diisopropylpropylene urea, N,N'-dibutylpropylene urea, N,N,N',N',N'',N''-hexamethylphosphoric acid triamide, 1,3,4-trimethyl-2-imidazolidinone, ethylene glycol dimethyl ether, ethylene glycol diethyl ether, ethylene glycol dipropyl ether, ethylene glycol diisopropyl ether, ethylene glycol dibutyl ether, diethylene glycol dimethyl ether, diethylene glycol diethyl ether, diethylene glycol dipropyl ether, diethylene glycol diisopropyl ether, diethylene glycol dibutyl ether, triethylene glycol dimethyl ether, triethylene glycol diethyl ether, triethylene glycol dipropyl ether, triethylene glycol diisopropyl ether, triethylene glycol dibutyl ether, tetraethylene glycol dimethyl ether, tetraethylene glycol diethyl ether, tetraethylene glycol dipropyl ether, tetraethylene glycol diisopropyl ether, tetraethylene glycol dibutyl ether, polyethylene glycol dimethyl ether, polyethylene glycoldiethyl ether, polyethylene glycol dipropyl ether, polyethylene glycol diisopropyl ether, and polyethylene glycol dibutyl ether.

4. The method as claimed in claim 2, wherein said reaction is carried out at a temperature of 80 to 180° C. and an acetylene pressure of 0.15 to 1.0 MPa (gauge pressure).

5. The method as claimed in claim 3, wherein said reaction is carried out at a temperature of 80 to 180° C. and an acetylene pressure of 0.15 to 1.0 MPa (gauge pressure).

* * * * *